United States Patent [19]

Krouskop

[11] Patent Number: 5,133,761
[45] Date of Patent: Jul. 28, 1992

[54] FINGER JOINT PROSTHESIS
[75] Inventor: Thomas A. Krouskop, Stafford, Tex.
[73] Assignee: Research Development Foundation, Carson City, Nev.
[21] Appl. No.: 713,892
[22] Filed: Jun. 12, 1991
[51] Int. Cl.$^5$ .............................................. A61F 2/42
[52] U.S. Cl. ........................................ 623/21; 623/16; 623/18
[58] Field of Search ................ 623/18, 21, 66, 16, 623/11, 13, 23

[56] References Cited

U.S. PATENT DOCUMENTS

| | | | |
|---|---|---|---|
| 3,526,906 | 9/1970 | Laszlo | 623/2 |
| 3,638,243 | 2/1972 | Campbell, Jr. et al. | 3/1 |
| 3,651,521 | 3/1972 | Devas | 623/21 |
| 3,808,606 | 5/1974 | Tronzo | 623/16 |
| 3,990,118 | 11/1976 | Strickland et al. | 623/18 |
| 4,011,603 | 3/1977 | Steffee | 623/21 |
| 4,231,121 | 11/1980 | Lewis | 3/1.91 |
| 4,304,011 | 12/1981 | Whelan, III | 3/1.91 |
| 4,459,708 | 7/1984 | Buttazzoni | 623/18 |
| 4,685,919 | 8/1987 | Niwa et al. | 623/21 |
| 4,750,768 | 7/1988 | Hermann et al. | 623/71 |
| 4,911,719 | 3/1990 | Merle | 623/18 |
| 4,944,758 | 7/1990 | Bekki et al. | 623/21 |

OTHER PUBLICATIONS

Bioceramics–Engineering in Medicine (Part I), Biomedical Materals Symposium No. 2, Hall, Hulbert, Levine, Young, pp. 42–47, 1972, John Wiley & Sons, Publishers.

Primary Examiner—Randall L. Green
Assistant Examiner—Dinh Nguyen
Attorney, Agent, or Firm—Fulbright & Jaworski

[57] ABSTRACT

An implantable carbon composite finger joint prosthesis having first and second members rotatably attached forming a single axis joint. The joint has a core which includes a three directionally woven high density carbon-carbon composite for strength, and a base for supporting stems which includes a porous vitreous carbon to promote bony tissue ingrowth, and the coacting joint surfaces include carbide which is wear resistant and will not support fibrous tissue.

5 Claims, 2 Drawing Sheets

FINGER JOINT PROSTHESIS

Background of the Invention

While many finger joint prosthesis have been designed and patented, the only finger joint prosthesis on the market with wide use is a silicone rubber device. A number of finger prosthesis have been developed made of metal, but have failed because the small sized metal parts that are required to interface with the bones of the finger are very subject to fatigue failures and are difficult to stabilize using bone cement. Acrylic cement used to hold the appliance in place often damages the bone and this results in loosening of the prosthesis and untimely failure of the device.

The present invention is directed to a finger joint prosthesis which is designed to be simple, strong, and easy to install. Furthermore, the present prosthesis is made from carbon so that the problem inherent with metal, strength that decreases with use, is eliminated. Varieties of carbon are selected to provide different properties at different parts of the prosthesis to accomplish advantageous results.

Summary

The present invention is directed to an implantable carbon, composite finger joint prosthesis comprising a first member and a second member rotatably attached forming a single axis joint. The first member includes a stem means for connecting the first member to bone. The first member also includes a smooth surfaced cylindrical female receptacle having an axially extending bore therethrough. The receptacle includes an opening parallel to the bore extending from one end of the receptacle to adjacent but spaced from the second end of the receptacle thereby forming a stop adjacent to the second end. The opening is of a constant angular width. Preferably the angular extent of the opening in the female receptacle is approximately 72°. The second member includes a stem means for connecting the second member to bone. The second member also includes a smooth surfaced cylindrical male member longitudinally and rotatably movable in the bore of the female receptacle.

Another further object of the present invention is wherein the longitudinal axis of the stem of the first member is offset from the longitudinal axis of the bore of the receptacle for providing greater stability.

Yet a still further object of the present invention is wherein the coacting surfaces of the female receptacle and the cylindrical male member are smooth and include carbide to provide a wear resistant articulating surface which does not need special lubrication and which will not support fibrous tissue attachment. Preferably the carbide is silicon carbide.

Still a further object of the present invention is wherein the surface of the stems includes a porous vitreous carbon that will promote ingrowth of calcified tissue that will stabilize the prosthesis after healing has occurred. Preferably the average pore size of the vitreous carbon is at least 300 micrometers.

Yet a still further object of the present invention is wherein the first member and the second member include a three direction woven high density carbon-carbon composite core.

Other and further objects, features, and advantages will be apparent from the following description of presently preferred embodiments of the invention, given for the purpose of disclosure, and taken in conjunction with the accompanying drawings.

DESCRIPTION OF THE PREFERRED EMBODIMENT

Figure 1:
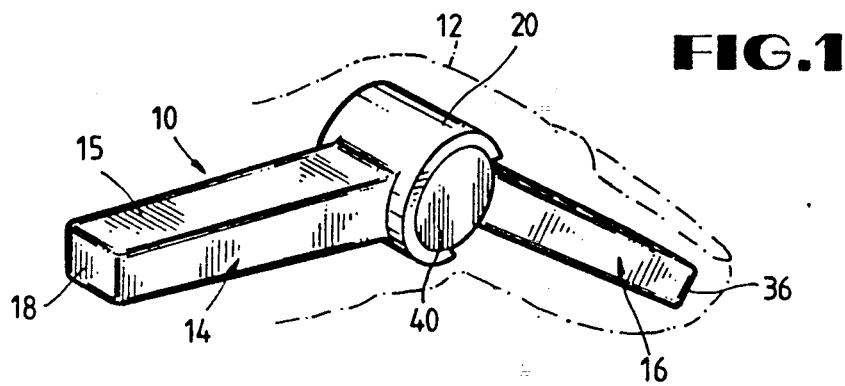
FIG. 1 is isometric elevational view of the prosthesis of the present invention implanted in a finger.
Figure 2:
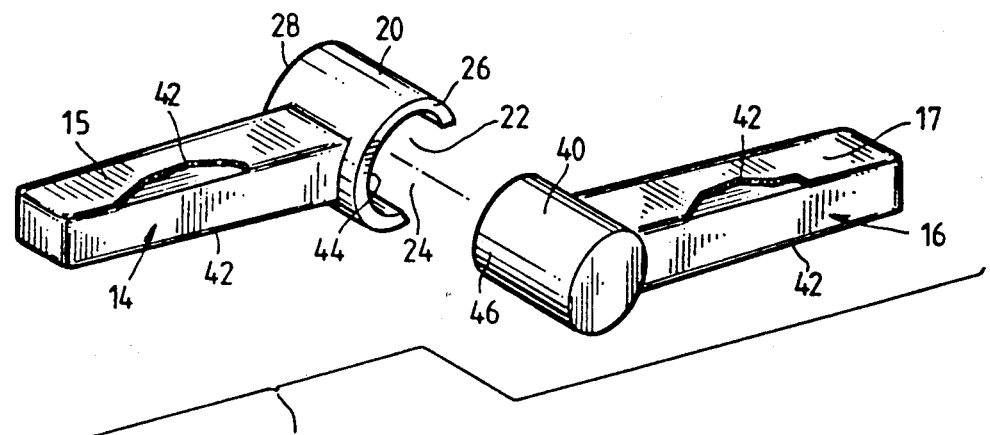
FIG. 2 is an exploded isometric view of the prosthesis of FIG. 1.
Figure 3:
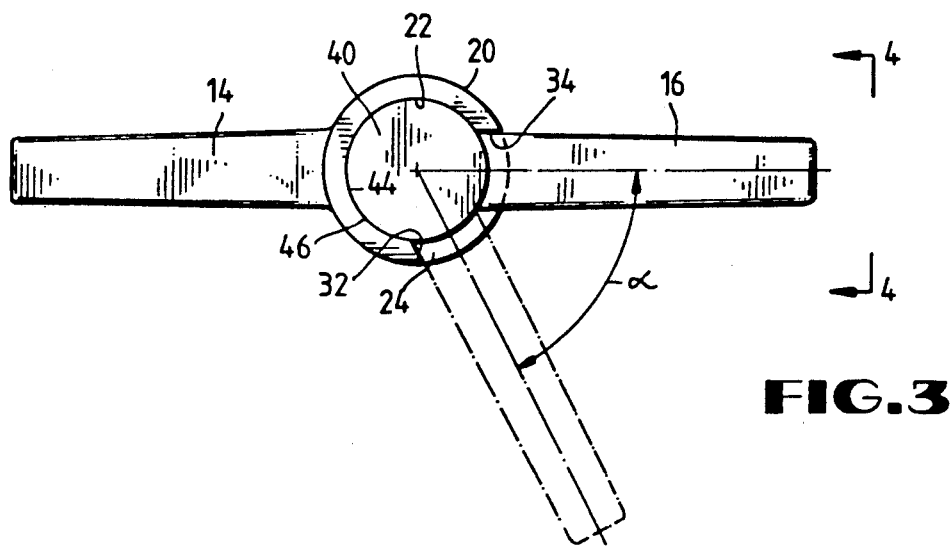
FIG. 3 is an elevational view of the prosthesis of the present invention showing the extent of rotative movement.

Referring now to the drawings, particularly to FIGS. 1–4, the reference 10 generally indicates the implantable carbon composite finger joint prosthesis of the present invention for implantation in a finger 12 shown in dotted out line in FIG. 1. The prosthesis generally includes a first member 14 and a second member 16 rotatably attached forming a single axis joint. The first member 14 includes a stem or intermedulary pin 15 such as a proximal stem having an end 18 for connection to a bone in the finger 12.

The first member 14 also includes a smooth cylindrical female receptacle 20 at its second end for forming a portion of the joint. The receptacle 20 includes an axially extending bore 22 therethrough and includes an opening 24 extending from one end 26 of the receptacle 20 to adjacent the second end 28 but spaced from the second end 28 thereby forming a stop shoulder 30 adjacent the second end 28. The opening 24 is bounded by a first edge 32 and a second edge 34 and the opening 22 is of a constant angular width.

The second member 16 includes an intermedulary pin or distal stem 17 means having an end 36 for connection to a bone in the finger 12. The second member 16 includes a smooth cylindrical male member 40 which is longitudinally and rotatably movable in the bore 22 of the female receptacle 20.

Figure 4:
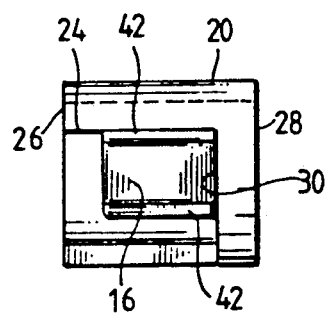
FIG. 4 is a cross-sectional view taken along the line 4—4 of FIG. 3.

It is to be noted that the cylindrical member 40 may be axially inserted in to the bore 22 of the receptacle 20 as the stem 17 moves into the opening 22 at the end 26 of the receptacle 20. When the edge of the stem 17 contacts the stop shoulder 30, as best seen in FIG. 4, the first and second members 14 and 16 are aligned for rotative member. The articulating joint formed by the receptacle 20 and cylindrical member 40 is designed to provide a suitable amount of flexure, for example at least 60° and preferably 72° as indicated by the angle alpha shown in FIG. 3. The second member 16 is symmetrical, thereby allowing the member 16 to be connected to the member 14 without error.

The base or core of the first member 14 and the second member 16 of the prosthesis 10 are made from a carbon-carbon composite material preferably a three directionally woven, high density carbon-carbon composite such as is available from Fiber Materials, Inc. Such a core provides strength and can be loaded to a porous surface layer of irtreous carbon that has a mechanical stiffness that is close to the stiffness of the calcified tissue that will ultimately be in contact with the prosthesis 10. Moreover, the stiffness of the composite can be designed to be very similar to that of the bone so that the deformations in the prosthesis will closely match the deformations in the surrounding bone. This allows the boundary between the finger bones and the joint prosthesis 10 to remain stable and the potential for the carbon to wear through the bone, as metal parts do, is minimized. Additionally, the carbon material will not corrode, is not subject to the development of half cell potentials within itself, and the prosthesis does not fatigue.

In addition, the exterior surfaces of the pins or stems 15 and 17, in particular the upper and lower surfaces are provided with layers 42 of a porous vitreous carbon, preferably with an average pore size of at least 300 micrometers. The thickness of the layers 42 may be one millimeter thick. The pore surfaces 42 permit bony tissue to ingrow and stabilize the prosthesis 10 to the bones and promote ingrowth of calcified tissue that will stabilize the device after healing has occurred. The layers 42 are secured to the carbon-carbon composite base or core by a conventional carbon adhesive.

The smooth articulating or coacting surfaces of the receptacle 20 and the cylindrical member 40, such as surfaces 44 and 46 respectively, are treated such as by conventional chemical reaction, so that they are a carbide, such as silicon carbide. Thus the coacting surfaces 44 and 46 are wear resistant, they do not require special lubrication, and in addition, because they are very smooth, they will not support fibrous tissue attachment.

Figure 5:
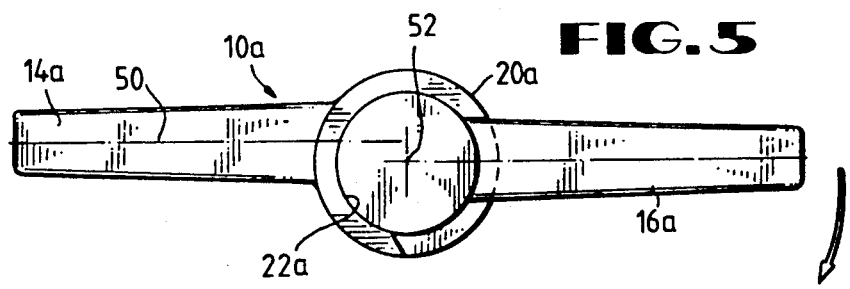
FIG. 5 is an elevational view of another embodiment of the present invention.

Other and further embodiments of the prosthesis of the present invention may be provided. Referring now to FIG. 5, another embodiment of the present invention is shown in which like parts to those in FIGS. 1-4 are similarly numbered with the addition of the suffix "a" and in FIG. 6 a further embodiment is shown in where like parts to those in FIGS. 1-4 are similarly numbered with the addition of the suffix "b".

In FIG. 5, the prosthesis 10a is generally similar to the prosthesis 10 with the exception that the longitudinal axis 50 of the first member 14a is offset from the longitudinal axis 52 of the bore 22a of the receptacle 20a. This provides greater stability and stress reduction in the female member 14 for the prosthesis 10a as compared with the prosthesis 10 because the male member 16 of the device cannot pull out of the member 14 when tensile loads are applied to the stems 15 and 17. The offset also provides a greater bearing area to resist tensile loadings and thus the stress in the member 14 are reduced in the region surrounding the male cylindrical member 40.

Figure 6:
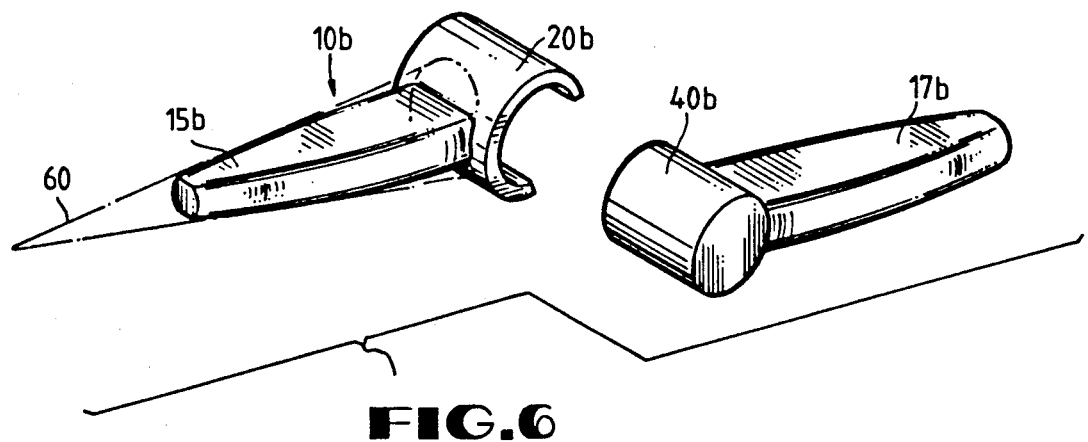
FIG. 6 is an exploded isometric view of still a further embodiment of the present invention.

As indicated, minor shaping of the intermedulary pins is possible to provide a good fit with the finger bones without adversely affecting the strength of the prosthesis. Referring now to FIG. 6, a prosthesis 10b is provided which is generally similar to the prosthesis 10 with the exception that the stems 15b and 17b are shaped out of cones 60, shown in dotted outline and flattened on the top and bottom to provide a stable high strength, but tapered stems 15b and 17b which more nearly match the deformations in the bones in which they are to be connected.

In use, the prosthesis 10, 10a, and 10b are designed to allow a surgeon to place the stems or pins of the prosthesis in prepared ends of the carpal bones and then by offsetting the bones, slipping the receptacle and coacting articulating cylindrical members together. Once the prosthesis is placed, the joint ligaments are used to provide stability for the prosthesis along with the stop 30 on the receptacle 20 to prevent axial disengagement of the joint. The prosthesis is inherently stable throughout the range of motion and cannot be pulled apart accidentally as in some types of ball and socket prosthesis, but does allow some lateral movement in response to large mechanical loads which could otherwise cause failure.

The present invention, therefore, is well adapted to carry out the objects and attain the ends and advantages mentioned as well as others inherent therein. While presently preferred embodiments of the invention have been given for the purpose of disclosure, numerous changes in the details of construction, and arrangements of parts, may be made without departing from the spirit of the invention, and the scope of the appended claims.

What is claimed is:

1. An implantable carbon composite finger joint prosthesis comprising, a first member and a second member rotatably attached forming a single axis joint, said first member including a stem means for connecting said first member to a bore in a bone, said first member including a cylindrical surface forming a female receptacle having first open and second closed ends and having an axial extending bore therethrough, said surface including an opening parallel to the axis extending from the first open end of the receptacle to adjacent but spaced from the second closed end of the receptacle thereby forming a stop adjacent the second closed end, said opening defining a constant angular extent, said second member including a stem means for connecting said second member to a bore in a bone, and said second member including a cylindrical male member longitudinally movable through the first end of the female receptacle and rotatively movable in the axial bore of the female receptacle.

2. The prosthesis of claim 1 wherein the angular extent of the opening is approximately 72°.

3. The prosthesis of claim 1 wherein the average pore size of the vitreous carbon is at least 300 micrometers.

4. The prosthesis of claim 1 wherein the first member and the second member includes a three directionally woven high density carbon-carbon composite, the stems include surfaces having a porous vitreous carbon, and the female receptacle and the cylindrical male member include coacting surfaces having carbide.

5. An implantable carbon composite finger joint comprising, a first member and a second member rotatably attached forming a single axis joint, said first member including a stem means for connecting said first member to a bore in a bone, said first member including a cylindrical surface forming a receptacle having first open and second closed ends and having an axial extending bore therethrough, said first end being open to the bore and said second end being closed forming a stop, said receptacle including an opening parallel to the axis extending from the open first end to the stop at the second end, said opening a constant angular extent of approximately 72°, said second member including a stem means for connecting said second member to a bore in a bone, and said second member including a cylindrical male member longitudinally movable through the first end of the female receptacle and rotatively movable in the axial bore of the female receptacle, the axial axis of the stem of the first stem of the first member is offset from the axial axis of the bore of the bore of the receptacle, and said stems include surfaces which include porous vitreous carbon.

* * * * *

UNITED STATES PATENT AND TRADEMARK OFFICE
CERTIFICATE OF CORRECTION

PATENT NO. : 5,133,761
DATED : July 28, 1992
INVENTOR(S) : Thomas A. Krouskop

It is certified that error appears in the above-indentified patent and that said Letters Patent is hereby corrected as shown below:

Column 2, beginning with line 66 and ending on line 67, delete "can be loaded to a porous surface layer of irtreous carbon that has a"

Signed and Sealed this

Seventh Day of May, 1996

Attest:

BRUCE LEHMAN

Attesting Officer   Commissioner of Patents and Trademarks